(12) United States Patent
Den Boer et al.

(10) Patent No.: US 6,303,390 B1
(45) Date of Patent: Oct. 16, 2001

(54) METHOD FOR ANTIGEN AND ANTIBODY DETERMINATION IN BLOODGROUP SEROLOGY

(75) Inventors: Pieter Johannes Den Boer, Leiden; Eric Marinus Maria Van der Donk, Nieuwegein; Ronald Victor Wilhelmus Van Eijk, Bunnik, all of (NL)

(73) Assignee: Stichting Sanquin Bloedvoorziening, Amsterdam (NL)

( * ) Notice: Subject to any disclaimer, the term of this patent is extended or adjusted under 35 U.S.C. 154(b) by 0 days.

(21) Appl. No.: 09/214,823

(22) PCT Filed: Jul. 9, 1997

(86) PCT No.: PCT/NL97/00402

§ 371 Date: Sep. 20, 1999

§ 102(e) Date: Sep. 20, 1999

(87) PCT Pub. No.: WO98/02752

PCT Pub. Date: Jan. 22, 1998

(30) Foreign Application Priority Data

Jul. 11, 1996 (NL) .................................................. 1003570

(51) Int. Cl.$^7$ ................................................. E01N 33/555
(52) U.S. Cl. ............................... 436/520; 435/5; 435/7.1; 435/7.25; 436/512; 436/513; 436/518; 436/521; 436/548; 436/16; 436/809; 436/810; 436/828
(58) Field of Search .............................. 435/5, 7.1, 7.25, 435/287.1; 436/512, 513, 518, 520, 521, 548, 16, 809, 810, 828, 177, 178; 422/56–59, 61, 101

(56) References Cited

U.S. PATENT DOCUMENTS

| | | | |
|---|---|---|---|
| 4,297,104 | * 10/1981 | Claude | 23/230 |
| 4,560,647 | * 12/1985 | Stocker | 435/5 |
| 4,585,623 | * 4/1986 | Chandler | 422/57 |

(List continued on next page.)

FOREIGN PATENT DOCUMENTS

| | | |
|---|---|---|
| 0 194 212 A1 | 9/1986 | (EP) . |
| 0 485 228 A1 | 5/1992 | (EP) . |
| 2 660 437 A1 | 10/1991 | (FR) . |
| WO 95 30904 A1 | 11/1985 | (WO) . |

OTHER PUBLICATIONS

Derwent abstracts in English language for FR 2 660 437 A and EP 194 212 A.

*Primary Examiner*—Long V. Le
*Assistant Examiner*—Pensee Do
(74) *Attorney, Agent, or Firm*—Hoffman & Baron, LLP

(57) ABSTRACT

Method and test kit for assaying in a sample an analyte which is a bloodgroup antigen present on erythrocytes or an antibody binding to such a bloodgroup antigen. To that end, the sample is treated with a reagent containing a binding partner for the analyte, so that a complex of bloodgroup antigen present on erythrocytes and antibody bound thereto is formed if the sample contains analyte. The analyte is a bloodgroup antigen present on erythrocytes, the analyte binding partner is an antibody capable of binding to the bloodgroup antigen and if the analyte is an antibody binding to a bloodgroup antigen, the analyte binding partner is the bloodgroup antigen present on erythrocytes. Erythrocytes, complex or non-complexed, are then separated from non-bound antibodies using a separation medium with a density higher than that of the liquid containing the antibodies but lower than the density of crythrocytes. Complexed erythrocytes are separated from non-complexed erythrocytes by binding complexed erythrocytes to a solid surface on which an immunoglobuilin-binding substance is immobilized and discharging non-complexed erythrocytes to a deepened zone of the reaction vessel. The result is then determined by detecting where the erythrocytes are located.

35 Claims, 1 Drawing Sheet

U.S. PATENT DOCUMENTS

| | | | |
|---|---|---|---|
| 4,608,231 | * | 8/1986 | Witty et al. .............................. 422/61 |
| 5,059,520 | * | 10/1991 | Furukawa et al. ................... 435/7.21 |
| 5,213,963 | * | 5/1993 | Uthemann ............................ 435/7.25 |
| 5,240,862 | * | 8/1993 | Koenhen et al. ..................... 436/178 |
| 5,312,628 | * | 5/1994 | Cohen et al. .......................... 424/88 |
| 5,512,432 | * | 4/1996 | Lapierre et al. .......................... 435/5 |
| 5,514,555 | * | 5/1996 | Springer et al. ..................... 435/7.24 |
| 5,552,325 | * | 9/1996 | Nochumson et al. ................ 436/177 |
| 5,652,148 | * | 7/1997 | Doshi et al. .......................... 436/178 |
| 5,665,558 | * | 9/1997 | Frame et al. ........................ 435/7.25 |
| 6,114,179 | * | 9/2000 | Lapierre et al. ...................... 436/518 |

* cited by examiner

METHOD FOR ANTIGEN AND ANTIBODY DETERMINATION IN BLOODGROUP SEROLOGY

FIELD OF THE INVENTION

The invention lies in the field of bloodgroup serology and relates more particularly to a method and a test kit for determining bloodgroup antigens, or antibodies directed thereto, in a sample.

BACKGROUND OF THE INVENTION

The purpose of bloodgroup assays and antibody examination in clinical work is often to obtain compatible erythrocyte preparations for transfusion. The invention concerns the detection and identification of antibodies and antigens and can be used for bloodgroup assay, antibody screening and identification, and performing cross tests. The test is based not on hemagglutination but on the solid-phase principle, without involving washing steps.

In a bloodgroup, specific antigenic determinants on the cell membrane are involved. The information for expressing bloodgroup antigens is fixed on a gene level and heritable. Bloodgroup antigens can give rise to the formation of antibodies. Specific antibodies to bloodgroup antigens are mostly formed after immunization with the corresponding antigen. An exception to this is formed by the so-called "naturally occurring" antibodies which without apparent immunization are demonstrable in the serum (anti-A and anti-B). The presence of antibodies plays an important role in blood transfusion, pregnancy and auto-immunity.

Antibodies can be classified in different ways:

1. xeno-antibodies, allo-antibodies and auto-antibodies;
2. regular and irregular antibodies;
3. naturally occurring antibodies;
4. complete (IgM) antibodies and incomplete (IgG) antibodies.

Blood transfusion reactions which are induced by allo-antibodies to erythrocytes are called hemolytic transfusion reactions because they are mostly accompanied by an often very strongly accelerated breakdown of erythrocytes. The point is therefore to prevent hemolytic transfusion reactions by careful bloodgroup examination.

Bloodgroup antibodies are nearly always immunoglobulins of the IgG type or the IgM type. The antigen-antibody interaction is dependent inter alia on ionic bonding, hydrogen bridges and hydrophobic effects (displacement of water). The strength of a binding between a binding site of an antibody and an epitope is designated as 'affinity'. Antibodies which are able to agglutinate erythrocytes under all conditions are called agglutinins or complete antibodies (mostly IgM). Antibodies which do bind to erythrocytes but give no agglutination (sensitization) are called incomplete antibodies (mostly IgG).

The detection of erythrocyte antigens and corresponding antibodies often takes place by means of agglutination reactions. Agglutination reactions can be allowed to take place in a physiological salt solution. In practice, this is not always optimal. A number of tests can be rendered more sensitive by using a number of aids, such as the use of medium having a low ionic strength (low ionic medium), proteolytic enzymes (e.g. bromelin, papain or ficin), polycations (e.g. polybrene), macromolecules (e.g. albumin), or polymers (e.g. polyethylene glycol, PEG).

An important and widely applied test is the antiglobulin or Coombs test. The antiglobulin test is based on the principle that erythrocytes loaded with, for instance, antibodies of the IgG type can be agglutinated by antiglobulin serum. This is the most important test for demonstrating incomplete antibodies. The antiglobulin test was described by Moreschi in 1908 (Zbl. Bakt 46: 49) and reintroduced in 1945 by Coombs et al. (Lancet 2: 15, Brit. J. Exp. Path. 26: 255). The test can be distinguished into three phases. The first phase is the sensitization phase. During this phase, antibodies bind to the corresponding antigen structures on the erythrocytes (sensitization of erythrocytes). When the binding is optimal, the second phase, viz. the washing phase, takes place. In this phase, all non-bound antibodies are removed from the incubation mixture. Insufficient removal of non-bound antibodies can lead to inactivation of the antiglobulin serum in that these antibodies bind to the antiglobulin. The third phase is the antiglobulin phase, in which antiglobulin is added to the washed sensitized cells, so that the sensitized cells are coupled to each other (agglutination of the erythrocytes).

There is a large variety of serological tests. The most important techniques at present are the tube method, the column test and tests in microtiter plates. A distinction can be made between techniques that are based on hemagglutination and techniques that are based on the solid-phase principle.

a. Tests based on agglutination:

The tube test is a widely used test which also allows prolonged incubations with antibodies. After the reaction with antibodies, the erythrocytes can be settled or be centrifuged to accelerate the agglutination reaction.

In performing the Coombs test, it is necessary, before adding the antiglobulin serum, to wash very thoroughly and frequently. The antigen-antibody reaction is evaluated by gently tapping the tube and then rotating the tube (tip and roll) so that any agglutinates that have formed are dislodged from the tube. The reading of the test must be done promptly by an experienced person and the result of the test cannot be preserved. Because the reading of the test occurs manually, its reproducibility is not optimal either. The disadvantage of this method is that it is difficult to automate.

As indicated, the washing step in the Coombs test takes up much time. Graham et al. (Transfusion 1982, 22: 408; P. L. Mollison, Blood transfusion in clinical medicine, Blackwell, Oxford, 1983, p. 512) developed a new principle which rendered the washing step redundant. This principle was used by Ortho Diagnostic Systems Inc. in a test system (Simwash). According to this system, erythrocytes are separated from the serum by means of a centrifugation step. The separation is based on the fact that the specific gravity of serum (1.03) is lower than that of erythrocytes (1.09). Now, if a mixture of cells and serum is applied on top of a layer of medium of a density between the density of the cells and that of the serum, the erythrocytes will be separated by a centrifugation step from the serum (containing the non-bound antibodies). Thus the erythrocytes are centrifuged from the original incubation mixture. In this way a triple or quadruple washing step is reduced to a single centrifugation step. Then the sensitized cells can be incubated with antiglobulin serum. However, the system proved not to be sensitive enough.

A further simplification of serological tests has been carried through by centrifuging the erythrocytes through a column of (Sephadex) gel or glass beads. The use of transparent, inert, solid particles for distinguishing agglutinates and non-agglutinates was already described by Dalton et al. in 1970 (Becton Dickinson & Co., U.S. Pat. No. 3,492,396). The system whereby gel material is used for the detection of erythrocyte-antibody reactions was described by LaPierre et al. (Transfusion 1990; 30: 109–113, European Patents 0 194 212 and 0 305 337). This system combines the principles of Simwash and the use of solid inert particles to discriminate between agglutinates and non-agglutinates. In this test system, use is made of small columns filled with Sephadex gel. Use can be made of columns not containing any antibodies (e.g. for reverse ABO typing). As a second possibility, a gel column can also contain antibodies which are directed to certain erythrocyte antigens (e.g. for typing). For the antiglobulin test, use is made of gel columns which contain antiglobulin serum. After an incubation the gel columns are centrifuged. In the case of a negative reaction, all erythrocytes will end up at the bottom of the tube; if the test is positive, the erythrocyte agglutinates will be caught on top of or in the gel. In the case of weak reactions, erythrocytes will sediment partly. A major advantage of this test is that in case of the antiglobulin test no washing steps are needed anymore. In fact, during the centrifugation a separation of erythrocytes and serum or plasma constituents takes place. A second advantage is the fact that the results of the test can be properly fixed. The test described is used by DiaMed AG (DiaMed-ID Microtyping System) and Diagast Laboratoires (Chromatest). A comparable system, Ortho Biovue System (Ortho Diagnostic Systems), utilizes glass beads instead of gel material as inert material to catch agglutinates which have formed. A disadvantage of these tests is that a special centrifuge is required for the correct performance of the test. Also, automatic reading of the test requires special reading equipment.

b. Tests based on the solid-phase principle:

Another approach is the use of the solid-phase principle as an alternative to direct and indirect agglutination reactions for bloodgroup assay, antibody screening, antibody identification and cross tests. Application and advantages of the use of solid-phase techniques in the areas mentioned have been described by Rosenfield (Abstracts, 15th Cong. Int. Soc. Blood Trans., Paris pp. 27–33, 1976; U.S. Pat. No. 4,275,053, 1981). Here, inter alia erythrocytes were used which were coupled to the surface of plastic tubes. More recently, systems have been described by Plapp et al. (Am. J. Clin. Path. 82: 719–721, 1984), Bayer et al. (U.S. Pat. No. 4,608,246, 1986), Rachel et al. (Transfusion 25: 24–26, 1985), Plapp et al. (The Lancet 1465–1466, 1986) and Uthemann et al. (U.S. Pat. No. 4,925,786, EP 363 510 and Transfusion 30: 114–116, 1990).

Microtiter plates in combination with the solid-phase principle are employed by, among others, Biotest AG (Solidscreen II for antibody diagnostics), Immucor Inc. (Immunocapture Capture-R systems for antibody screening and identification) and CLB (Microtype for typing erythrocyte antigens). The Capture-R system utilizes a solid phase to which membranes of erythrocytes are bound. During the incubation with serum or plasma from donors or patients, erythrocyte-specific antibodies can bind to these membranes. After the washing phase, whereby the non-bound antibodies are removed, indicator erythrocytes are added. Indicator erythrocytes are sensitized erythrocytes to which anti-human immunoglobulin is bound. Instead, it is also possible to use synthetic particles (spheres) to which anti-human immunoglobulin is bound. If in the plasma or serum antibodies were present, bridging will arise between the antibody bound to the solid phase and the indicator erythrocytes. This principle has also been described by Bayer et al. (U.S. Pat. No. 4,608,246) for antibody screening and identification. In addition to this system, Bayer et al. also describe the performance of a cross test, in which use is made of anti-IgG coupled to the solid phase. Both unknown blood components (plasma and erythrocytes) are put together in the well so that sensitization of the erythrocytes can take place. However, in this set-up, inactivation of the anti-IgG bound to the solid phase will arise and sensitized cells will not be able to bind to the solid phase anymore, unless after the sensitization phase first a washing phase is carried out. Recently, Llopis et al. have described a variant of the solid phase test, intended for screening and identifying antibodies (Vox Sanguinis 1996; 70: 152–156). In this method a monolayer of test erythrocytes (erythrocytes with a known antigen composition) is made in a U-bottom well of a microtiter plate, whereafter incubation takes place with serum which includes antibodies. This is followed by five manual washing steps. The detection takes place by addition of polyspecific anti-human globulin (IgG+C3d) and indicator erythrocytes (these are, in this case, erythrocytes which are sensitized with anti-D antibodies). Finally, a centrifugation step takes place again. Disadvantages of this test are, among others, the limited life of the monolayer of test erythrocytes and the repeated manual washing of the monolayer after incubation with antibodies.

Solidscreen of Biotest AG (antibody screening and identification) and Microtype of CLB (antigen typing) utilize a solid phase to which (inter alia) human IgG is bound. In the wells the incubation of erythrocytes and plasma, serum or antibody-containing reagent takes place. If corresponding antibodies are present, sensitization of erythrocytes takes place. The sensitized cells are then washed to remove non-bound antibodies. Detection takes place by addition of anti-human globulin serum and a centrifugation step, so that the sensitized cells are bound via the antiglobulin to the IgG on the solid phase. In these systems, positive reactions are characterized by a monolayer of erythrocytes on the solid phase. In the case of negative results, no monolayer is formed, but the cells form a so-called "button" in the U-bottom microtiter plate well.

A disadvantage of the known solid-phase microtiter plate tests is that frequent washing is required in order to remove the non-bound antibodies. This washing typically proceeds manually, entailing the continued possibility that patient serum or plasma (potentially infectious material) is spread during the washing steps. A cycle from the washing phase comprises in succession: centrifugation, removal supernatant, addition of medium and resuspension of the erythrocytes. This time-consuming cycle must be repeated a number of times in order to remove all non-bound antibodies. Automation of this washing procedure is possible. This involves one centrifugation step, whereafter supernatant medium is carefully removed, whereafter an amount of medium is applied to the pellet of erythrocytes, in such a manner that no resuspension of the erythrocytes take place. This step must be repeated about six times. Normal microtiter plate washing devices (such as ELISA washers) are not suitable for this washing step. For that purpose, a special washing device is needed. After the washing phase all washing liquid is removed and antiglobulin serum is added. Then the erythrocytes are resuspended and the microtiter plate is centrifuged. The sensitized erythrocytes will be bound to the IgG of the solid phase through the antiglobulin. Non-sensitized erythrocytes will not be able to bind to the solid phase and will be found as button in the U-bottom well. It goes without saying that incomplete washing away of antibodies leads to inactivation of the antiglobulin, so that sensitized erythrocytes cannot bind via the antiglobulin to the solid phase anymore, and will result in a so-called false-negative reaction. The advantage is that automatic processing of results is possible. An important point in this connection is that during the washing phase no loss or only slight loss of cells may arise, since this can present problems when (automatically) reading the test.

The solid-phase tests are not limited to microtiter plates. Pernell (Sanofi Pasteur, EP 0 594 506) describes an affinity gel test in which an immunoglobulin-binding substance (such as protein A, protein G or anti-human globulin) is immobilized on the gel. Incubation of erythrocytes and antibodies occurs above the gel. After this incubation phase centrifugation of the gel column takes place. If antibodies are bound to the erythrocytes, these sensitized erythrocytes will bind to the immunoglobulin-binding gel material and will hence bind to the upper part of the gel column. Cells to which no antibodies are bound will not be bound and end up on the bottom of the column. This principle of binding of sensitized cells to a solid-phase has previously been described by Pharmacia (Cell Affinity Chromatography; Uppsala, Sweden; 1984). Pharmacia therein describes the purification of erythrocytes on the basis of the presence or absence of certain bloodgroup antigens using protein A sepharose 6 MB. Erythrocytes with the A antigen on the surface (bloodgroup A erythrocytes) to which anti-A antibodies are bound can be separated, by binding to the gel material mentioned (via protein A), from erythrocytes which do not possess the A-antigen. The test described by Sanofi Pasteur is therefore a combination of this principle and the centrifugation step for separation of erythrocytes which may or may not be sensitized and non-bound antibodies as used in Simwash (Ortho) and different column systems (Diagast, DiaMed and Ortho). A disadvantage of the test as described by Sanofi Pasteur, where the ligands described are protein G or an antiglobulin, is that no complement factors are bound, as protein G only binds IgG antibodies. In serology, however, erythrocytes loaded with complement factors are also of interest (for instance in demonstrating complement-binding antibodies such as anti-Jk antibodies). In the Sanofi Pasteur gel test, therefore, if these antibodies are to be demonstrated with a high sensitivity, anti-complement too will have to be immobilized on the gel material. The disadvantage of the use of protein A as immunoglobulin-binding material is that antibodies of the type IgG3 cannot be demonstrated (as protein A only binds the IgG subclasses IgG1, IgG2 and IgG4). These can be clinically relevant, however.

Another variant of a solid-phase test has recently been described by Den Boer et al. (WO 95/30904). In this test, which is suitable, for example, for antibody screening and antibody identification, the solid phase is a porous membrane on which an immunoglobulin-binding substance is immobilized. This membrane, which contains pores sufficiently large to pass erythrocytes, is placed in a tube or cup (of, for instance, a microtiter plate). The membrane is disposed in a medium of high density. Incubation of, for instance, erythrocytes and an antibody-containing sample takes place above this medium, in such a manner that no contact can occur between the antibody-containing incubation mixture and the solid phase. After the incubation phase referred to, a centrifugation step takes place. The antibody-containing sample remains above the medium, erythrocytes will be centrifuged downwards. Thus a separation of erythrocytes and non-bound antibodies is achieved. Due to the centrifugation step, the erythrocytes will move to the solid phase, the sensitized erythrocytes will bind to it, while non-sensitized ones will pass through the solid phase. A disadvantage of this test is that reading must be done at two different levels, as the non-sensitized cells are on the bottom of the test system whilst the sensitized cells are on the solid phase which is at some distance above the bottom of the test system.

BRIEF SUMMARY OF THE INVENTION

The present invention provides a method for assaying in a sample an analyte selected from a bloodgroup antigen present on erythrocytes or an antibody binding to such a bloodgroup antigen, comprising treatment of the sample in an incubation zone of a reaction vessel with a reagent containing an analyte binding partner, which analyte binding partner, in the case where the analyte is a bloodgroup antigen present on erythrocytes, is an antibody capable of binding to the bloodgroup antigen, and, in the case where the analyte is an antibody binding to a bloodgroup antigen, is the bloodgroup antigen present on erythrocytes, wherein in the incubation zone a complex of bloodgroup antigen present on erythrocytes and antibody bound thereto is formed if the sample contains the analyte, further comprising separation of erythrocytes, complexed or non-complexed, from non-bound antibodies, using a separation medium, located beneath the incubation zone in the reaction vessel, with a density higher than that of the liquid containing the antibodies but lower than the density of erythrocytes, whereby erythrocytes pass through the separation medium and non-bound antibodies remain in the incubation zone, separation of complexed erythrocytes from non-complexed erythrocytes by binding complexed erythrocytes in an immobilization zone of the reaction vessel to an immunoglobulin-binding substance immobilized in this zone, and discharging non-complexed erythrocytes to a collection zone of the reaction vessel, and detection of erythrocytes in the immobilization zone and/or collection zone.

The present invention also provides a test kit suitable for use in a method for assaying an analyte in a sample, the analyte being a bloodgroup antigen present on erythrocytes or an antibody binding to such a bloodgroup antigen, comprising:

(i) a reagent containing an analyte binding partner which, in the case where the analyte is a bloodgroup antigen present on erythrocytes, is an antibody capable of binding to the bloodgroup antigen, and, in the case where the analyte is an antibody binding to a bloodgroup antigen, is the bloodgroup antigen present on erythrocytes, (ii) a reaction vessel comprising an incubation zone, an immobilization zone and a collection zone, with an immunoglobulin-binding substance immobilized in the immobilization zone, and (iii) a separation medium with a density lower than the density of erythrocytes but higher than the density of an antibody-containing liquid.

DETAILED DESCRIPTION OF THE INVENTION

Figure 3:
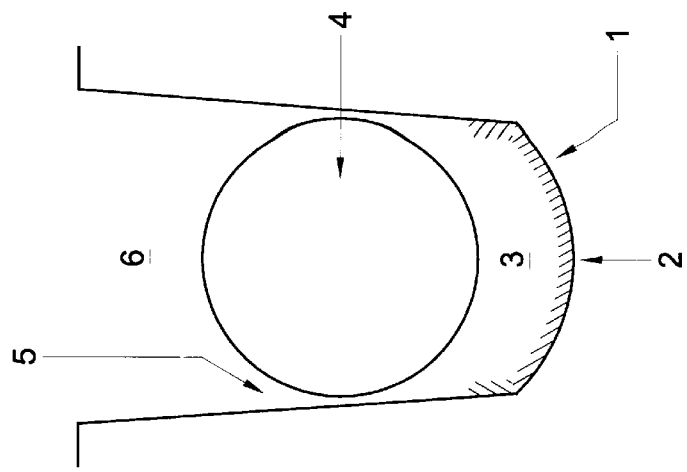
FIG. 3: this figure also shows a reaction vessel with a U-bottom well of a microtiter plate (strip). Functioning as immunoglobulin-binding immobilization zone is the bottom (1), in particular the higher portion thereof, whilst the deeper center of the bottom serves as collection zone (2). Disposed above the immobilization zone, in the embodiment shown here, is a sphere (4). This sphere can be made of glass as well as of plastic. Disposed in the area between the sphere and the immobilization zone is the high-density medium (3) functioning as separation medium. Incubation of erythrocytes and antibodies takes place above the sphere: the incubation zone (6). In case of a glass sphere, it is loosely clamped approximately halfway in the reaction vessel or use can be made of recesses in the reaction vessel on which the sphere rests (such as present, for instance, in the reaction vessels of NUNC microtiter plate strips (StarWell, NUNC, Denmark). In the case of a plastic sphere, the same can be done, but if the plastic has a lower density than the separation medium, an option is to have the sphere float approximately halfway in the reaction vessel. The presence of the sphere makes it easy to mix and incubate erythrocytes and antibody-containing sample, or conversely, antibody and erythrocyte-containing sample. After the incubation period a centrifugation step takes place, in such a manner that erythrocytes pass to the side of the sphere and through the space (5) between the sphere and the wall of the reaction vessel. Non-sensitized erythrocytes will thereupon move along the wall of the immobilization zone to the deepened portion of the reaction vessel, again functioning as collection zone. A negative reaction becomes visible by a cumulation of cells in the center of the reaction vessel. Sensitized erythrocytes will bind to the wall in the immobilization zone. A positive reaction becomes visible by binding of erythrocytes in the immobilization zone of the reaction vessel.

The invention concerns a method for demonstrating antibodies and antigens, the application of this method lying mainly in the field of bloodgroup serology: bloodgroup assay, antibody screening and antibody identification, and cross tests.

In the invention, a solid phase is used, on which immunoglobulin-binding substances are immobilized. Functioning as such is a portion of the surface of a reaction vessel in which the test is being conducted. The immunoglobulin-binding portion of the (inside) surface of the reaction vessel is herein designated as the 'immobilization zone'. Preferably, use is made of so-called U-bottom or V-bottom wells of microtiter plates, or strips thereof. The microtiter plates, or strips thereof, can be made of plastic (e.g. polystyrene, polypropylene, etc.). The immunoglobulin-binding substance can be immobilized on the entire bottom of the reaction vessel, but need not be present in the deepest portion of the bottom because this portion functions as the 'collection zone' for non-complexed erythrocytes. The immunoglobulin-binding substance can also be immobilized in an area above the bottom of the reaction vessel on the inside wall of the reaction vessel.

According to the invention, sensitized erythrocytes can be bound directly to the solid phase (the immobilization zone) without using an additional washing step or cycle of washing steps. Disposed above the immunoglobulin-binding solid phase is a liquid medium, designated here as the 'separation medium', with a density intermediate the density of erythrocytes and the density of the antibody-containing liquid. This layer is of importance for the invention because the presence of this layer renders unnecessary a separate washing phase for separating non-bound antibodies from the erythrocytes, sensitized or not. Above this layer of separation medium; the incubation of erythrocytes and antibodies takes place. The area located above the separation medium is herein designated as the 'incubation zone'.

After the incubation phase a centrifugation phase takes place, in such a manner that the erythrocytes are centrifuged through the high-density separation medium. The antibody-containing liquid remains above this high-density medium. So in this manner the erythrocytes are separated from non-bound antibodies, coming, for instance, from the serum or plasma. A cycle of washing steps is thus rendered superfluous and loss of erythrocytes is impossible. Partly owing to the absence of a separate washing procedure, the test takes considerably less time. The use of a convex or concave surface in the incubation compartment will result in the erythrocytes being led, during the centrifugation phase, to the elevated portion of the immobilization zone, whereafter the cells are led along the solid phase and can bind to it. By this manner of carrying out the test, a relatively prolonged contact of the erythrocytes with the solid phase is guaranteed, so that sensitized erythrocytes can bind optimally to the solid phase. The invention means an improvement of the current microtiter plate solid-phase principle.

The invention accordingly provides a method for assaying in a sample an analyte selected from a bloodgroup antigen present on erythrocytes or an antibody binding to such a bloodgroup antigen, comprising treatment of the sample in an incubation zone of a reaction vessel with a reagent containing an analyte binding partner, which analyte binding partner, in the case where the analyte is a bloodgroup antigen present on erythrocytes, is an antibody capable of binding to the bloodgroup antigen, and, in the case where the analyte is an antibody binding to a bloodgroup antigen, is the bloodgroup antigen present on erythrocytes, wherein in the incubation zone a complex of bloodgroup antigen present on erythrocytes and antibody bound thereto is formed if the sample contains the analyte, further comprising separation of erythrocytes, complexed or non-complexed, from non-bound antibodies, using a separation medium, located below the incubation zone in the reaction vessel, of a density higher than that of the liquid containing the antibodies but lower than the density of erythrocytes, whereby erythrocytes pass through the separation medium and non-bound antibodies remain in the incubation zone, separation of complexed erythrocytes from non-complexed erythrocytes by binding completed erythrocytes in an immobilization zone of the reaction vessel to an immunoglobulin-binding substance immobilized in this zone, and discharging non-complexed erythrocytes to a collection zone of the reaction vessel, and detection of erythrocytes in the immobilization zone and/or collection zone.

The invention further provides a test kit suitable for use in a method for assaying an analyte in a sample, the analyte being a bloodgroup antigen present on erythrocytes or an antibody binding to such a bloodgroup antigen, comprising:

(i) a reagent containing an analyte binding partner which, in the case where the analyte is a bloodgroup antigen present on erythrocytes, is an antibody capable of binding to the bloodgroup antigen, and, in the case where the analyte is an antibody binding to a bloodgroup antigen, is the bloodgroup antigen present on erythrocytes, (ii) a reaction vessel comprising an incubation zone, an immobilization zone and a collection zone, with an immunoglobulin-binding substance immobilized in the immobilization zone, and (iii) a separation medium with a density lower than the density of erythrocytes but higher than the density of an antibody-containing liquid.

The invention described here has the following advantages over existing techniques:

1) the sensitivity of the test is high owing to the use of high-affinity immunoglobulin-binding substances combined with the solid phase technique.
2) by leading the erythrocytes along the solid phase a prolonged and better contact of all erythrocytes with the solid phase is obtained, so that a better binding is effected.
3) no wash step is needed for removing non-bound immunoglobulins, so that no loss of cells can occur.
4) the test takes little time.
5) no separate indicator-erythrocyte system is needed for the detection of antibody-antigen reactions which have occurred.
6) the assay can be performed on existing equipment.
7) reading and interpreting the test can be simply carried out visually but can also be readily automated, also because reading occurs at one level.
8) it is a user-friendly, uniform system.
9) in addition to immunoglobulin-binding substances, anti-complement antibodies can be used. The fact is that certain bloodgroup antibodies cause the presence of complement factors on the membrane of erythrocytes. Anti-complement antibodies can bind to these complement factors (a certain type of serum proteins) present on the erythrocytes. Therefore the immobilization zone could include an immunoglobulin-binding substance in combination with one or more anti-complement antibodies.

The invention described can be applied to the current tests within bloodgroup serology, including screen tests for antibodies, identification of antibodies, cross-tests, antigen assay, bloodgroup assay and antibody titration. The invention can, for instance, be used for determining the following bloodgroup antigens and antibodies to those antigens: ABO, Kell (K), cellano (k), Duffy ($Fy^a$ and $Fy^b$), Kidd ($Jk^a$ and $Jk^b$), Lutheran ($Lu^a$ and $Lu^b$), the Rhesus system (D, E, e, C, c), MNS, Lewis ($Le^a$ and $Le^b$), etc.

By way of example, the invention can be used for the following assays:

Tests in which use is made of an antiserum of known specificity and erythrocytes of unknown antigen composition (bloodgroup assay, antigen assay).

Tests in which use is made of sera having therein an unknown antibody or unknown antibodies and erythrocytes having a known antigen composition (antibody screening, antibody identification). Here, often use is made of a panel of erythrocytes of known antigen composition. In addition, the test can also be used for the detection of auto-antibodies. In this case, on the erythrocytes antibodies are already bound to the corresponding antigens. So the erythrocytes are already sensitized and can bind directly to the solid phase.

Tests performed in accordance with the present invention are all based on the same principle: erythrocytes to which antibodies are bound (sensitized erythrocytes) can bind to the solid phase, unlike non-sensitized erythrocytes.

The sample will typically consist of blood or a material derived therefrom, such as blood plasma, blood serum or a blood fraction, for instance erythrocytes isolated from blood. However, since the invention can also be used for other purposes, such as the selection of hybridomas which produce monoclonal antibodies that bind to a bloodgroup antigen, the sample can also consist of materials of a different kind, for instance of a supernatant of a hybridoma.

It is essential that during the incubation of antibodies with erythrocytes and the centrifugation step there be no contact between this incubation mixture and the solid phase, which is why a medium of high density has been applied to the solid phase. Separation between this medium and the incubation mixture can be realized for practical purposes by the use of, for instance, a porous membrane, but also by means of a separation surface provided with recesses. In addition, the choice of immunoglobulin-binding substances and the choice of the material to increase the density of the medium are of importance. These points will be briefly elucidated here.

a. Immunoglobulin-binding substances.

The choice from immunoglobulin-binding substances that can be immobilized on the solid phase is large. Useful are, for instance, polyclonal or monoclonal antibodies directed to immunoglobulin G (IgG), immunoglobulin A (IgA) and/or immunoglobulin M (IgM). In order to increase the sensitivity, or to detect a widest possible range of antibodies, it is also possible to immobilize a combination of several immunoglobulin-binding substances on the solid phase. Also, antibodies to the complement system can be used.

It is also possible to use immunoglobulin-binding substances of a different origin, for instance from bacteria. Immunoglobulin-binding bacterial proteins are used, for instance, in immunology, biochemistry, and biotechnology. A number of immunoglobulin-binding proteins have been isolated and characterized.

mThe most important are protein A (Forsgren et al. J. Immunol. 1966; 97: 822) and protein G (Björck et al. J. Immunol. 1984;133: 969; Reis et al. J. Immunol. 132: 3091). Recently, two other bacterial proteins capable of binding immunoglobulins have been described, viz. protein L for binding to the light chain of IgG, IgA and IgM (Infect. Immun. 58: 1217–1222; 1990, J. Immunol. Methods 164: 33–40, 1993 and J. Biol. Chem. 264: 19740–19746; 1989) and protein H with a high affinity for the heavy chain and Fc fragments of immunoglobulins (Åkesson et al. Mol. Immunol. 27: 523–531; 1990). The use of these proteins and recombinant products derived therefrom, such as protein A/G (ImmunoPure Immobilized Protein A/G, Pierce) and L/G (Kihlberg et al. J. Biol Chem. 267: 25583; 1992) and the use of genetically modified bacteriophages (A. S. Kang et al., Proc. Natl. Acad. Sci. USA 88: 4363–4366) in immunohematology and in particular for antibody and antigen assays in bloodgroup serology are further described in WO 95/30904.

For the tests involving IgG antibodies (antibody identification, antibody screening and cross tests) use can be made of a solid phase with an IgG-binding substance with a high affinity, so that optimum binding of sensitized cells to a solid phase is ensured. As immunoglobulin-binding substance, in addition to anti-human immunoglobulin, protein G can be used again. A solid phase on which immunoglobulin-binding substances are immobilized that bind both IgA, IgG and IgM is most ideal, since in that case the widest range of antibody specificities can be demonstrated. The immunoglobulin-binding substance can be immobilized on the solid phase both by means of absorption and by means of covalent binding. The immunoglobulin-binding solid phase can be freeze-dried by means of freeze protecting substances and stabilized and then stored dry.

b. Substances for increasing the density of the medium can be many kinds of substances, including, e.g., albumin, dextran, Ficoll, iodixanol, sodium diatrizoate, Percoll, etc.

For carrying out the test it is preferred to use a test system of microtiter plate format (with the possibility of performing single and multiple tests) where the bottom of the test wells has a so-called U- or V-shape. On this U- or V-shaped bottom, the imunoglobulin-binding complex or an immunoglobulin-binding substance is immobilized. It can consist of, for instance, 1) mono or polyspecific anti-IgG (of the IgG or the IgM type), 2) human immunoglobulin G (IgG) having coupled thereto anti-human IgG to obtain a longer arm for better binding of sensitized erythrocytes or 3) bacterial proteins, such as protein G.

Figure 2:
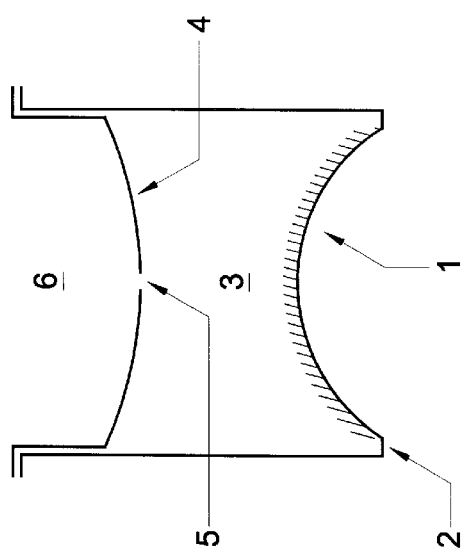
FIG. 2: here use was made of a reaction vessel with a bottom whose center is higher than the circumference or periphery. The immunoglobulin-binding immobilization zone (1) is located centrally. The deepened portion of the bottom, which serves as collection zone (2), is located at the edge in this case. In the embodiment shown a concave separation surface (4) was used. Provided centrally in this separation surface is a recess or passage (5). After mixing and incubation of erythrocytes and antibodies the erythrocytes will, by centrifugation, be transported to the middle of this surface, leave the incubation zone (6) through the recess and pass the high-density separation medium (3), whereupon the immobilization zone is reached. In case of a negative reaction (non-sensitized erythrocytes) the cells will end up in the deepened portion of the reaction vessel, which becomes visible by a ring of cells around the immobilization zone. Again, a positive reaction becomes visible by binding of erythrocytes to the wall of the immobilization zone, so in particular in the central portion of the bottom.
Figure 1:
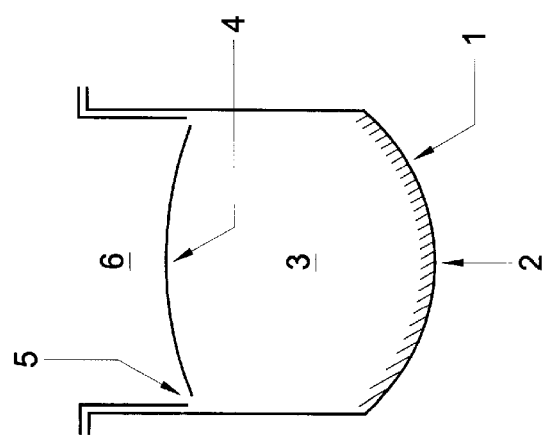
FIG. 1: this figure shows as reaction vessel a U-bottom well of a microtiter plate. As immunoglobulin-binding immobilization zone functions the bottom (1), in particular the higher portions thereof, whilst the deeper center of the bottom serves as the collection zone (2). Disposed above the immobilization zone, in the embodiment shown here, is a convex separation surface (4) with recesses or passages (5) at the circumference. In the area between the immobilization zone and this separation surface there is a high-density medium (3) functioning as separation medium. Incubation of erythrocyte and antibodies takes place above this separation surface: the incubation zone (6). The presence of the separation surface makes it easy to mix and incubate erythrocytes and antibody-containing sample, or conversely, antibody and erythrocyte-containing sample. After the incubation period a centrifugation step takes place, in such a manner that erythrocytes pass to the side of the separation surface and through the recesses. Non-sensitized erythrocytes will subsequently travel along the wall of the immobilization zone to the deepened portion of the reaction vessel, which functions as collection zone. A negative reaction becomes visible by a cumulation of cells in the center of the reaction vessel. Sensitized erythrocytes will bind to the wall in the immobilization zone. A positive reaction becomes visible by binding of erythrocytes in the immobilization zone of the reaction vessel.

Provided on this solid phase is a layer of separation medium of a density higher than that of the antibody-containing liquid but lower than that of erythrocytes. This layer is of importance to the invention as the presence of this layer provides that no separate washing step is necessary to separate non-bound antibodies from the (sensitized) erythrocytes. The incubation of erythrocytes and antibodies can take place in different ways, e.g., directly on the separation medium of high density, or in a compartment provided at the underside with a membrane (of, for instance, polycarbonate or polyethylene terephthalate) or preferably (because of a greater potential contact surface per cell by passing the erythrocytes along the solid phase) on a convex (FIGS. 1 and 3) or concave (FIG. 2) separation surface provided with (a) recess(es) on the sides and in the middle, respectively. After the incubation phase in which cells and antibodies can bind, the erythrocytes, which may or may not be sensitized, are separated by centrifugation (via, for instance, the recesses) through the separation medium, from non-bound antibodies and transported to the solid phase, whereafter the sensitized cells will adhere to the solid phase, while the non-sensitized cells are transported to the deepened portion of the solid phase. Detection of the bound cells on the solid phase can simply be done visually or also automatically.

EXAMPLES

The invention will now be further explained in and by the following examples. It is of importance to see, however, that these examples are given for illustrative purposes and illuminate the enablement of the invention but in no way constitute the definitive conditions of the different assay methods.

Example 1

As solid phase, U-bottom microtiter plate strips (Maxisorp, NUNC, Denmark) were used, on which human intramuscular IgG (CLB, Amsterdam, Netherlands) was coated (5 $\mu$g/ml IgG in 100 mM sodium carbonate buffer, pH 9.0, over 16 hours at room temperature). Coating was followed by washing 5× with phosphate-buffered saline solution (PBS, pH 7.4) and blocking with an albumin solution (1% bovine serum albumin in PBS) to prevent a specific binding. Then 50 $\mu$l anti-human IgG (monospecific anti-human IgG serum, CLB, Amsterdam, Netherlands) was coupled. After 4 hours of incubation, washing was done 4× with PBS. To the solid phase thus obtained, 150 $\mu$l high-density medium (15% iodixanol in preservative liquid for erythrocytes (CLB, Amsterdam, Netherlands)) was applied.

To this layer of medium, 50 $\mu$l 1.5% Coombs Control Cells (CCC; CLB, Amsterdam, Netherlands) was applied in the presence of 50 $\mu$l AB serum or 50 $\mu$l PBS. The CCC are erythrocytes with bloodgroup $0^+$ (i.e. bloodgroup 0, rhesus D positive) which are sensitized with anti-D antibodies. As control were used $0^+$ cells which are not loaded with antibodies. Then followed centrifugation for 5 min at 40 g, followed by 5 min at 200 g. Table 1 summarizes the results.

TABLE 1

| incubations | result |
| --- | --- |
| CCC + PBS | + |
| $0^+$ + PBS | – |
| CCC + AB serum | + |
| $0^+$ + AB serum | – |

CCC upon centrifugation yield an even layer of cells over the solid phase (+; positive reaction), $0^+$ cells give a button of cells in the central, deepened portion of the solid phase (–; negative reaction).

The test of the CCC in the presence of AB serum indicates that the erythrocytes were effectively separated from non-bound antibodies. If the antibodies had not remained above the separation layer, the solid phase would have been inactivated and the CCC would have given a false-negative reaction.

Example 2

Typing of Erythrocytes for Rhesus Antigens

The solid phase system as described in Example 1 was used. 25 $\mu$l 3% erythrocyte suspension (in preservative liquid), incubated with, respectively, 25 $\mu$l anti-C, anti-c, anti-E, anti-e and anti-D reagent (polyclonal reagents, CLB, Amsterdam, Netherlands), was applied to the separation medium. Each antiserum was employed with a positive as well as a negative cell. A positive cell is an erythrocyte which possesses the corresponding antigen, a negative cell does not possess the corresponding antigen. Then followed incubation in an oven for 20 min at 37° C. This was followed by centrifugation as described in Example 1. The results are shown in Table 2. A CCC, incubated with AB serum, was included as positive control. The first column lists the specificity of the antibody used, the second column lists the phenotype of the erythrocyte in question. The third column lists the result of the assay, a positive reaction was an even pink layer of cells on the solid phase, a negative reaction a "button" of erythrocytes in the center of the well.

TABLE 2

| antibody | phenotype | erythrocyte | result |
|---|---|---|---|
| anti-C | $R_ZR_1$ | $C^+c^-$ | pos |
| anti-C | $R_2R_2$ | $C^-c^+$ | neg |
| anti-c | $R_ZR_1$ | $C^+c^-$ | neg |
| anti-c | $R_2R_2$ | $C^-c^+$ | pos |
| anti-E | $R_2R_2$ | $E^+e^-$ | pos |
| anti-E | r'r | $E^-e^+$ | neg |
| anti-e | $R_2R_2$ | $E^+e^-$ | neg |
| anti-e | r'r | $E^-e^+$ | pos |
| anti-D | $R_2R_2$ | D | pos |
| anti-D | r"r | d | neg |
| AB serum | Coombs Control Cell | | pos |

Example 3

Experiments as described in Example 2 were carried out for the Kell-bloodgroup system. 25 $\mu$l 3% erythrocyte suspension (in preservative liquid), incubated with, respectively, 25 $\mu$l anti-K, anti-k and anti-Kp$^a$ (polyclonal IgG antiserum, CLB, Amsterdam, Netherlands), was applied to the separation medium and then incubated in an oven at 37° C. for 20 min. Here too, per antibody specificity a positive cell and a negative cell were tested. Then centrifugation as described in Example 1 was performed. The results are summarized in Table 3. An AB serum-incubated CCC was included as positive control. The table lists in succession the specificity of the antibody used, the phenotype of the erythrocyte in question and the result of the test. Anti-K and anti-k sensitized erythrocytes yielded an even layer of erythrocytes on the solid phase. The anti-Kp$^a$ sensitized cell yielded a partial coverage of the solid phase.

TABLE 3

| antibody specificity | phenotype erythrocyte | result |
|---|---|---|
| anti-K | $K^-k^+$ | neg |
| anti-K | $K^+k^+$ | pos |
| anti-k | $K^-k^+$ | pos |
| anti-Kp$^a$ | $Kp^{a-}$ | neg |
| anti-Kp$^a$ | $Kp^{a+}$ | pos |

Example 4

Use was made of the solid phase as described in Example 1. Test erythrocytes with phenotype $Fy^{a+b-}$ were taken. From these, a 0.75% suspension was made in a LISS solution (3 mM sodium phosphate, 61 mM sodium chloride and 240 mM glycine; pH 6.6). As antibody-containing sample, patient serum was used which contained anti-Fy$^a$ antibody (in the so-called PEG test this sample gave a weakly positive (2+) reaction). This sample was diluted in AB serum, a number of dilutions thereof were tested. 75 $\mu$l erythrocyte suspension was incubated with 75 $\mu$l (diluted) patient serum at 37° C. for 20 min and then centrifuged. Table 4 summarizes the results.

TABLE 4

| dilution | result |
|---|---|
| undiluted anti-Fy$^a$ | positive<br>cells spread over entire solid phase |
| diluted 1:2 in AB serum | positive<br>cells spread over virtually entire solid phase |
| diluted 1:4 in AB serum | weakly positive<br>cells spread over portion of the solid phase |
| AB serum alone | negative<br>cells in the center of the well |

Example 5

As solid phase, U-bottom microtiter plate strips (Maxisorp, NUNC, Denmark) were used, on which human intramuscular IgG (CLB, Amsterdam, Netherlands) was coated (5 $\mu$g/ml IgG in 100 mM sodium carbonate buffer, pH 9.0, over 16 hours at room temperature). Coating was followed by washing 5× with phosphate-buffered saline solution (PBS, pH 7.4) and blocking with an albumin solution (1% bovine serum albumin in PBS) to prevent a specific binding. Then 50 $\mu$l anti-human IgG (monospecific anti-human IgG serum, CLB, Amsterdam, Netherlands) was coupled. After 4 hours of incubation, washing was done 4× with PBS. To the solid phase thus obtained, 50 $\mu$l high-density medium was applied. Then per reaction vessel a glass sphere was loosely clamped approximately halfway. On top thereof, 50 $\mu$l 1.5% Coombs Control Cells (CCC, CLB, Amsterdam, Netherlands) was applied in the presence of 50 $\mu$l AB serum or 50 $\mu$l PBS. As control, 0$^+$ cells were used. Then centrifugation took place for 5 min at 40×g, followed by 5 min at 100×g. Table 5 lists the results.

TABLE 5

| incubations | result |
|---|---|
| CCC + PBS | + |
| 0$^+$ + PBS | − |
| CCC + AB serum | + |
| 0$^+$ + AB serum | − |

The reaction patterns are the same as those described in Example 1 for both CCC and 0$^+$ erythrocytes.

What is claimed is:

1. An improved method for assaying an analyte in a sample, wherein the analyte is selected from the group consisting of a blood group antigen present on erythrocytes and an antibody that binds to a blood group antigen present on erythrocytes;

wherein the method comprises treating the sample present in a liquid in an incubation zone of a reaction vessel with a reagent containing an analyte binding partner, wherein the analyte binding partner, in the case where the analyte is a blood group antigen present on erythrocytes is an antibody that binds to the blood group antigen, and in the case where the analyte is an antibody that binds to a blood group antigen present on erythrocytes is the blood group antigen present on erythrocytes;

wherein the reaction vessel comprises an incubation zone, an immobilization zone and a collection zone; and wherein a complex of blood group antigen present on erythrocytes and antibody bound thereto is formed in the incubation zone if the reagent contains an antibody that binds to the blood group antigen present in the sample, or if the sample contains an antibody that binds to a blood group antigen present in the reagent;

wherein the method further comprises separating the complex, from unbound erythrocytes that have not formed a complex, and detecting the result;

wherein the improvement comprises separating the erythrocytes, whether in the form of a complex or unbound, into a separation medium, the separation medium having a density higher than the density of the liquid containing the sample, but lower than the density of erythrocytes;

whereby the erythrocytes pass into the separation medium and the antibodies that are not bound to an erythrocyte remain in the liquid containing the sample in the incubation zone;

wherein the complex is separated from the unbound erythrocytes by binding the complex to an immunoglobulin-binding substance immobilized in an immobilization zone of the reaction vessel and discharging the unbound erythrocytes to a collection zone of the reaction vessel; and either detecting the erythrocytes in the immobilization zone or the erythrocytes in the collection zone; or detecting the erythrocytes in each of the immobilization zone and the collection zone.

2. The method according to claim 1, wherein the sample comprises blood, blood plasma, blood serum, a blood fraction or a supernatant of a hybridoma.

3. The method according to claim 1, wherein the incubation zone is located above the immobilization zone.

4. The method according to claim 1, wherein the collection zone is located below the immobilization zone.

5. The method according to claim 1, wherein the separation medium is present in a region below the incubation zone.

6. The method according to claim 1, wherein the separation medium is present in a region above the immobilization zone.

7. The method according to claim 1, wherein the reaction vessel is a microtiter plate well.

8. The method according to claim 7, wherein the microtiter plate well has a concave bottom.

9. The method according to claim 7, wherein the microtiter plate well has a convex bottom, the immunoglobulin-binding substance is immobilized at least to an upper portion of the bottom of the plate well, and the lower portion of the bottom of the plate well functions as the collection zone.

10. The method according to claim 7, wherein the immunoglobulin-binding substance is immobilized at least to an upper portion of the bottom of the plate well and the lower portion of the bottom of the plate well functions as the collection zone.

11. The method according to claim 8, wherein the concave bottom of the microtiter plate is U-shaped or V-shaped in cross section.

12. The method according to claim 1, wherein the separation medium contains a density increasing substance.

13. The method according to claim 12 wherein the density increasing substance is selected from the group consisting of albumin, dextran, Ficoll, iodixanol, sodium diatrizoate and Percoll.

14. The method according to claim 1, wherein the separation medium contains an erythrocyte preservative liquid.

15. The method according to claim 1, wherein the incubation of sample with reagent is carried out directly on the separation medium.

16. The method according to claim 1, wherein the incubation of sample with reagent is carried out in the incubation zone, wherein the incubation zone is separated from the separation medium by an element selected from the group consisting of a porous membrane, a bottom provided with one or more openings, and a spherical object.

17. The method according to claim 16, wherein the porous membrane is a plastic membrane.

18. The method according to claim 17, wherein the plastic membrane is a polycarbonate membrane or a polyethylene terephthalate membrane.

19. The method according to claim 17, wherein the incubation zone has a bottom provided with one or more passages at the periphery.

20. The method according to claim 17, wherein the incubation zone has a bottom provided with one or more centrally located passages.

21. The method according to claim 1, wherein the separating of erythrocytes and non-bound antibodies and the separating of the complex and the unbound erythrocytes is by centrifugation.

22. The method according to claim 21, wherein the separating of the complex and unbound erythrocytes is carried out by centrifugation at a higher centrifugal force than the centrifugal force in the separating of erythrocytes and non-bound antibodies.

23. The method according to claim 1, wherein the immunoglobulin-binding substance is an immunoglobulin-binding bacterial protein.

24. The method according to claim 23, wherein the immunoglobulin-binding bacterial protein is selected from the group consisting of protein A, protein G, protein L and protein H.

25. The method according to claim 1, wherein the immunoglobulin-binding substance is a recombinant protein with immunoglobulin-binding properties.

26. The method according to claim 25, wherein the recombinant protein with immunoglobulin-binding properties is protein L/G or protein A/G.

27. The method according to claim 1, wherein the immunoglobulin-binding substance is a monoclonal antibody.

28. The method according to claim 27, wherein the monoclonal antibody specifically binds an immunoglobulin selected from the group consisting of an IgG, an IgA and an IgM.

29. The method according to claim 1, wherein the immunoglobulin-binding substance is a polyclonal antibody.

30. The method according to claim 29, wherein the polyclonal antibody specifically binds an immunoglobulin selected from the group consisting of an IgG, an IgA and an IgM.

31. The method according to claim 1, wherein the immunoglobulin-binding substance is bound in the immobilization zone to the wall of the reaction vessel through a coupling means.

32. The method according to claim 31, wherein coupling means comprises an immunoglobulin.

33. The method according to claim 1, wherein the analyte is a blood group antigen present on erythrocytes.

34. The method according to claim 1, wherein the analyte is an antibody binding to a blood group antigen.

35. The method according to claim 1, wherein a cross-test is carried out in that erythrocytes of an unknown blood group antigen composition and antibodies of an unknown blood group specificity are used.

* * * * *

UNITED STATES PATENT AND TRADEMARK OFFICE
CERTIFICATE OF CORRECTION

PATENT NO. : 6,303,390 B1  
DATED : January 15, 2002  
INVENTOR(S) : Den Boer et al.

Page 1 of 1

It is certified that error appears in the above-identified patent and that said Letters Patent is hereby corrected as shown below:

Title page,  
In *Attorney, Agent*, or *Firm* now reads "Hoffman & Baron, LLP" this should read  
-- Hoffmann & Baron, LLP --  
ABSTRACT,  
Now reads "density of crythrocytes" should read -- density of erythrocytes --

Column 11,  
Line 1, now reads "mThe most important are protein A..." should read  
-- The most important are protein A... --  
Line 42, now reads "..., the imunoglobulin-binding complex..." should read  
-- ..., the immunoglobulin-binding complex... --

Signed and Sealed this

Ninth Day of April, 2002

Attest:

JAMES E. ROGAN  
*Attesting Officer*     *Director of the United States Patent and Trademark Office*